United States Patent [19]

Gillis et al.

[11] 4,284,600
[45] * Aug. 18, 1981

[54] METHOD FOR BIOHAZARD STEAM STERILIZATION

[75] Inventors: John R. Gillis, Harborcreek; Peter Miraldi, Erie, both of Pa.; Marius X. Stavers, Scotch Plains, N.J.

[73] Assignee: American Sterilizer Company, Erie, Pa.

[ * ] Notice: The portion of the term of this patent subsequent to Aug. 28, 1996, has been disclaimed.

[21] Appl. No.: 100,739

[22] Filed: Dec. 6, 1979

[51] Int. Cl.³ .......................... A61L 2/06; A61L 2/26
[52] U.S. Cl. .................................... 422/26; 422/109; 422/111
[58] Field of Search ................. 422/26, 109, 111, 119, 422/292, 295, 298, 299

[56] References Cited

U.S. PATENT DOCUMENTS

| 3,454,353 | 7/1969 | Bjork | 422/295 |
| 3,980,131 | 9/1976 | Perle et al. | 422/295 |
| 4,166,096 | 8/1979 | Gillis et al. | 422/299 |

FOREIGN PATENT DOCUMENTS 1027368  4/1958  Fed. Rep. of Germany .

Primary Examiner—Bradley Garris
Attorney, Agent, or Firm—Charles L. Lovercheck

[57] ABSTRACT

A method and apparatus for sterilizing highly infectious material. The sterilizer incorporates an inner chamber having no drain line and having a reservoir created by low dams at the bottom of the inner chamber at each end for collecting condensate during the sterilizing cycle. The chamber has a steam jacket. Water for sterilizing can be introduced into the chamber at the time the chamber is loaded.

5 Claims, 5 Drawing Figures

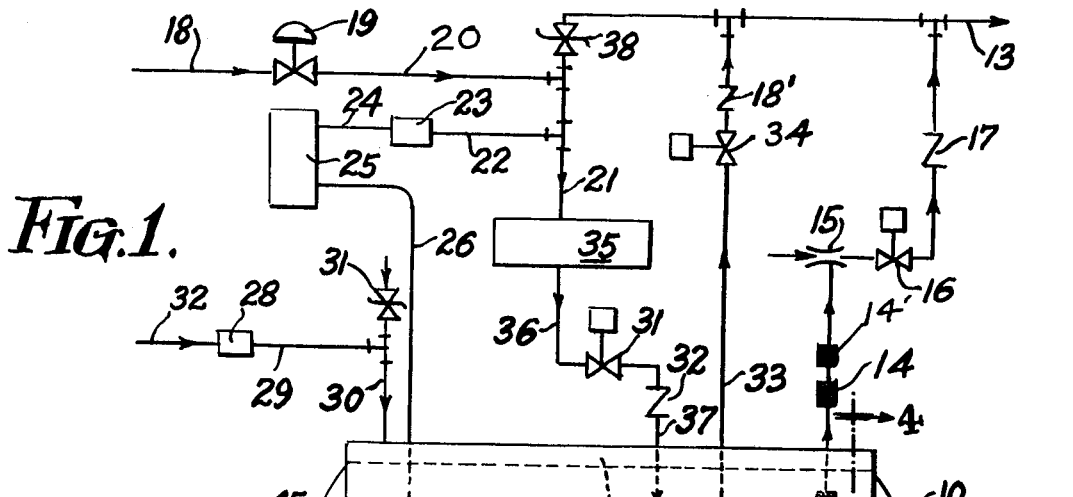
Fig.1.
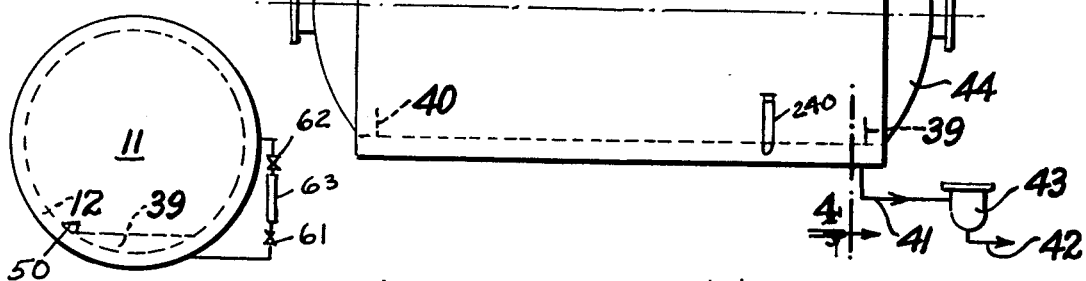
Fig.4.
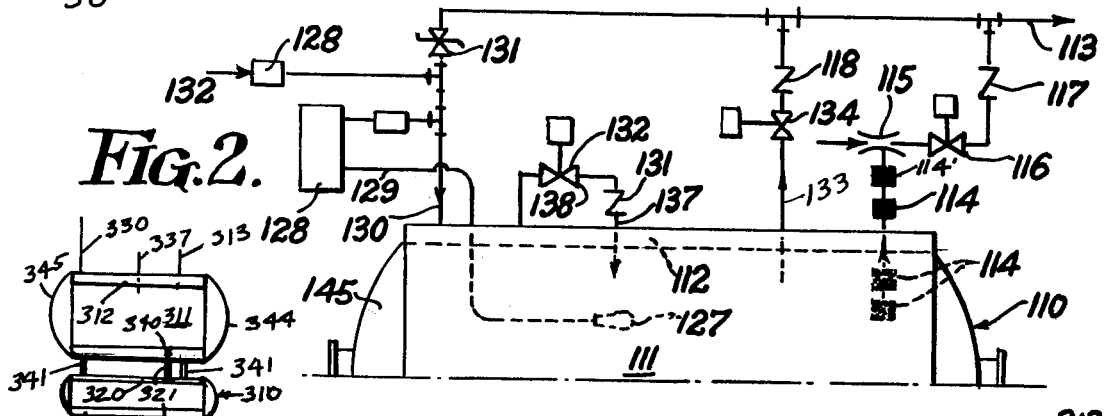
Fig.2.
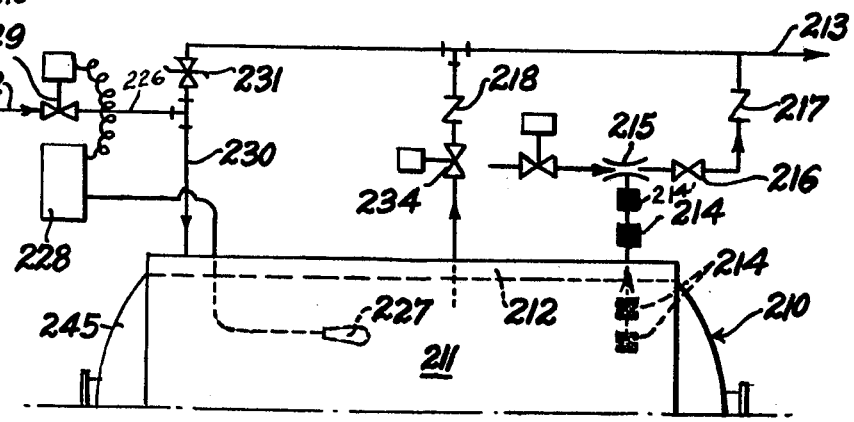
Fig.5.
Fig.3.

METHOD FOR BIOHAZARD STEAM STERILIZATION

GENERAL DESCRIPTION OF THE INVENTION

Any discharge from the sterilizing chamber prior to complete sterilization will contaminate drain lines and receiving areas and presents a significant problem. When standard sterilizers have been used, all discharges from the sterilizer went to a "kill" tank. Such discharges had to remain in isolation or be sterilized. Cumbersome apparatus and procedures resulted. The concept disclosed herein avoids such cumbersome procedures and provides means for readily sterilizing highly infectious materials. In effect, there is no discharge from the chamber which is not biologically safe.

REFERENCE TO PRIOR ART

The following United State patents indicate the state of the art in connection with steam sterilizers of the general type disclosed herein. However, these patents do not disclose the particular invention herein described:

U.S. Pat. Nos. 2,526,974—Schipanski;
U.S. Pat. Nos. 2,548,691—Vischer, Jr.;
U.S. Pat. Nos. 3,065,509—Vischer, Jr.;
U.S. Pat. Nos. 3,338,663—Beecher, et al;
U.S. Pat. Nos. 3,454,353—Bjork;
U.S. Pat. Nos. 3,481,692—Linder;
U.S. Pat. Nos. 3,604,895—MacKay.

OBJECTS OF THE INVENTION

It is an object of the invention to provide a sterilizer having a bio-retentive filter in series with the chamber.

Another object of the invention is to provide a steam sterilizer having the chamber and jacket isolated from each other through a one-way check valve.

Another object of the invention is to provide a steam sterilizer having a pressure switch control in the steam supply line to maintain the isolated jacket steam pressure equal to or greater than the chamber pressure.

Another object of the invention is to provide a steam jacket to the sterilizer chamber wherein the jacket is totally isolated from the chamber to supply a constant desired heat to the chamber.

Another object of the invention is to provide a steam sterilizer wherein steam may be generated by the chamber itself by adding water to the chamber prior to the sterilization cycle. The heat from the jacket generates the steam so that no external source of steam is needed.

With the above and the other objects in view, the present invention consists of the combination and arrangement of parts hereinafter more fully described, illustrated in the accompanying drawings and more particularly pointed out in the appended claims, it being understood that changes may be made in the form, size, proportions and minor details of construction without departing from the spirit or sacrificing any of the advantages of the invention.

GENERAL DESCRIPTION OF THE DRAWINGS

FIG. 1 is a schematic view of a sterilizer and control circuit according to the invention.

FIG. 2 is a partial, schematic view of another embodiment of the invention.

FIG. 3 is a partial view similar to FIG. 2 of a third embodiment of the invention.

FIG. 4 is a cross-sectional view taken on Line 4—4 of FIG. 1.

FIG. 5 is a schematic view of another embodiment of the invention.

DETAILED DESCRIPTION OF THE DRAWINGS

Now, with more particular reference to the drawings, the embodiment in FIG. 1 may be referred to as the external steam source method and shows a sterilizer and control circuit indicated generally at 10 having a chamber 11 with jacket 12. The chamber has no drain line.

An exhaust 13 is provided, which may exhaust into the atmosphere. The exhaust is connected through filters 14 and 14', which may be bacteria retentive filters, and through the vacuum source 15 and solenoid operated valve 16 and through check valve 17 to the exhaust 13.

Another exhaust connection is connected through line 33 and chamber exhaust valve 34 and check valve 18' to the exhaust line 13.

An external steam supply 18 is connected through pressure regulator 19 to the line 20 and then through external heat source 35 and line 36 and valve 31 and spring loaded check valve 32 to the chamber connection 37.

Pressure switch 23 is connected through line 22 to line 21 and to line 24 to control 25, which is, in turn, connected through line 26 to the temperature bulb 27. Heat for the jacket 12 is connected from line 32' and pressure regulator 28 to line 29 and line 30 to the jacket. A safety valve 31' is connected to lines 29 and 30. Likewise, valve 38 is connected to line 20.

The chamber has the dams 39 and 40 supported at each end inside which condensate collects as it drains down along the side of the chamber and forms basins to collect the condensate and allows it to boil off instead of running out of the chamber door when the door is opened presenting a hazard.

The dams can be made of a strip of sheet material one-inch wide for a small sterilizer on edge, welded to the chamber forming a reservoir sufficient to collect condensate that condenses on the inside of the chamber and runs down into the reservoir. The condensate then boils off instead of draining out as in the usual sterilizer.

The jacket has a drain line 41 connected to the drain 42 by way of the steam trap 43. The chamber is shown with an openable door 44 at one end and a similar door 45 at the other end through which the chamber can be loaded.

A typical cycle which can be carried out by the embodiment of the invention shown in FIG. 1 is: (1) establish an initial vacuum of 27 inches mercury using the air injector 15 as the vacuum source; (2) back-fill the chamber with steam to the desired pressure controlled by the control 25, (3) expose the product for the desired time period; and (4) exhaust the chamber and remove the articles being sterilized.

Now, with regard to the embodiment of the invention shown in FIG. 2, which may be referred to as the jacket steam source method, the sterilizer is indicated generally at 110 having a chamber 111 with jacket 112. The chamber is connected through filters 114 and 114' and through the vacuum source 115 which may be an air ejector of a type familiar to those skilled in the art and through the solenoid valve 116 and check valve 117 to the exhaust 113. In like manner, the line 133 is connected to the inside of the chamber through the chamber exhaust valve 134 and check valve 118 to exhaust 113. Steam connection 137 through the chamber is connected through the spring loaded check valve 131 and air-operated steam valve 132′ from the jacket connection 138.

Steam to the chamber is connected from the steam source 132 through the pressure switch 128 to the jacket connection 130. Safety valve 131′ connects the steam to the exhaust 113 in the case of over pressure.

The embodiment of the invention shown in FIG. 3 is referred to as the external steam source method. Sterilizer 210 has chamber 211 with jacket 212. Water is put in the chamber 211 and when it is boiled with the goods in the sterilizer and the steam from source 232 connected through valve 229 to the jacket line 230, the temperature of the chamber will be sensed by the temperature bulb 227 connected to control 228 and actuator valve 229 through line 249. Safety valve 231 protects the system against over pressure.

The embodiment of FIG. 3 will have a dam at each end of the chamber similar to the dam 39 and 40 in the embodiment shown in FIG. 1. The sterilizing cycle carried out in the embodiment of FIG. 2 can be much the same as that carried out by the embodiment of FIG. 1.

The sterilizer shown in the embodiment of FIG. 2 is known as a jacket steam source.

Water may be put into the chamber 211 initially when the chamber is loaded with the goods to be sterilized, and steam from the source 232 is connected through the valve 229 to the jacket line 230. The temperature of the chamber is sensed by the temperature bulb 227. The control 228 senses the chamber temperature through temperature bulb 227 and actuates the valve 229 through the line 249 thereby admitting steam from source 232 to the line 230 and thence to the jacket. Safety valve 231 protects the steam jacket against over pressure. The solenoid valve 234 connected the chamber through the check valve 218 to the exhaust line 213. Sight glass 240 indicates when water has inadvertently accumulated so that the door will be opened with care.

The chamber 211 will have a dam at each end thereof similar to the dams 39 and 40 in the embodiment of FIG. 1.

A sterilizer cycle with the machine disclosed herein can operate with or without an initial evacuation. Operation without an initial evacuation would be dependent on the capability of the chamber to withstand the pressure—a high pressure chamber (above 50psi) would be required if all air within the chamber after loading were to be entrapped and remain in the chamber during the sterilizing cycle. Air pressure is added to the saturated steam pressure (the latter being dependent on the desired sterilizing temperature).

Sterilizing can be carried out at standard steam sterilizing temperature, generally 250° F. or 270° F.

For more practical operation with the average sterilizing chamber at least a portion of the air is removed by an air ejector at the start of the cycle. The conventional air ejector operating on an empty chamber can draw down to 27″ Hg (vacuum). However, if liquids are being sterilized, there is a practical trade-off on the initial evacuation since the liquids will evaporate more readily as the pressure is taken down. Therefore, in practice, the sterilizer may be initially evacuated to vacuum levels of 10″ to 20″ Hg. Final total pressure, after adding saturated steam, can then be readily handled with the average chamber and safety valve equipment.

Considering this initial evacuation, it should be noted that a bio-retentive filter (highly efficient) is located at the chamber so that any of the air initially evacuated is filtered to be safe for atmospheric discharge. The bio-retentive filter is itself sterilized by the sterilizing cycle so that any infectious materials which were retained by the filter are sterilized during the cycle.

The air ejector system is set up so that the air ejector and the line between the inlet and outlet control valves are also sterilized. Therefore it is possible to locate the bio-retentive filter beyond the ejector toward the control valve on the discharge side, since the entire line will be sterilized during the sterilizing cycle.

As mentioned above, the steam source is connected to the isolated jacket only; a solenoid controlled valve in a line between the jacket and the chamber controls flow of steam to the chamber. The line from the jacket to the chamber also includes a one-way check valve so that contamination of the jacket is precluded.

As a further safety precaution in preventing contamination of the jacket, a pressure switch maintains the pressure in the jacket equal to or above the pressure in the chamber.

Temperature in the chamber is held at the desired level under the control of a temperature bulb within the chamber. The safety valve is on the jacket; therefore, any emergency discharge will be from a non-contaminated area. Location of the safety valve on the jacket rather than the chamber should meet boiler safety requirements since the only direct steam supply is to the jacket.

There is no drain on the chamber itself. Initial condensate from heating up the jacket can be removed without fear of contamination and, preferably, this is done before start of a sterilizing cycle.

After initial evacuation (if any), the chamber is backfilled with steam to the desired pressure to establish the desired saturated steam sterilizing temperature. This sterilizing temperature is maintained throughout the desired exposure time.

The load, and air remaining in the chamber, are heated by the condensation of steam; both are held to the desired temperature for the desired time. Any condensate within the chamber is gathered by the chamber dam.

After sterilization is completed, the chamber is vented before opening the sterilizing door. Substantially all, or a major portion, of the condensate gathered by the chamber dam will flash off during this exhaust. Since any condensate has been sterilized during the sterilizing cycle there is no danger of contamination in this flash-off.

Water sensor switch 50 inside the chamber may be connected to an alarm to warn the operator should hot water be present in the chamber to prevent door opening and injury from burns due to hot water. A quick close valve 61 and another quick close valve 62 will isolate the sight glass 63 should it break for additional safety.

The embodiment of the invention shown in FIG. 5, shows a sterilizing chamber 311 having closed ends 344 and 345 and having a steam jacket 312 for saturated steam. The steam supply 330 supplies saturated steam to the jacket similar to the manner in which the steam supply 32 supplies steam to the jacket in the embodiment of FIG. 1. The saturated steam is supplied to the chamber 311 through steam line 337, which is similar to line 37 in FIG. 1. Exhaust line 313 is provided also as the exhaust 13 in FIG. 1 and similar controls will be provided.

The condensate chamber 339 is supported on sterilizing chamber and has a jacket 320, which is connected to the jacket 312 through line 341. The interior of the chamber 311 is connected to the interior of chamber 339 through the line 321. When saturated steam is connected to the jacket 312 to heat the chamber 311, it, likewise, flows through lines 341 and into the jacket 320 of chamber 339.

When the chamber 311 is first loaded with materials to be sterilized and saturated steam is turned on through line 337, some of the steam may condense in the chamber 311. The line 340 will drain this condensate into chamber 339 where it will be evaporated into steam by the heat from the saturated steam in the jacket 320 and the evaporated condensate will flow back into the chamber 311 in the form of steam and, therefore, will not drain away into a repository where it may infect other objects.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A method of sterilizing comprising,
providing a chamber having no drain line, said chamber having a steam line with a first check valve in said steam line,
an opening above the bottom of said chamber with an evacuating means connected thereto.
and a second check valve and filter connected in series between said evacuating means and said opening,
loading said chamber with highly infectious material to be sterilized,
evacuating said chamber and said filter through said opening through said filter and through said second check valve to a subatmosphere pressure by said evacuating means, admitting steam to said chamber and raising the temperature of said chamber to sterilizing temperature,
maintaining said sterilizing temperature in said chamber for a period of time sufficient to accomplish sterilization,
and removing said material from said chamber.

2. The method recited in claim 1 wherein said chamber has a jacket and steam is connected to said jacket and means is provided to allow steam to flow from said jacket through a third check valve to said chamber thereby providing heating means for said chamber.

3. The method recited in claim 2 wherein a valve controlled by the temperature of said chamber is connected in series with said steam line to said jacket.

4. The method recited in claim 3 wherein said jacket is connected to said chamber through said first check valve preventing the flow of steam from said chamber to said jacket,
but allowing steam to flow from said jacket to said chamber.

5. The method recited in claim 1 wherein a reservoir is provided at the bottom of said chamber and a sight glass is connected to the outside of said chamber for indicating whether or not condensate is disposed in said reservoir,
thereby warning the operator not to open said chamber when condensate is present in said reservoir.

* * * * *